United States Patent [19]

Lai et al.

[11] Patent Number: 5,189,173
[45] Date of Patent: Feb. 23, 1993

[54] ALKYLATED POLYALKYLENE POLYAMINES AND PROCESS FOR SELECTIVE ALKYLATION

[75] Inventors: John T. Lai, Broadview Heights; Pyong-nae Son, Akron, both of Ohio

[73] Assignee: The BFGoodrich Company, Akron, Ohio

[21] Appl. No.: 318,047

[22] Filed: Mar. 2, 1989

Related U.S. Application Data

[63] Continuation-in-part of Ser. No. 103,779, Oct. 2, 1987, abandoned, which is a continuation-in-part of Ser. No. 786,765, Oct. 11, 1985, abandoned, which is a continuation-in-part of Ser. No. 664,901, Oct. 26, 1984, Pat. No. 4,547,538, which is a continuation-in-part of Ser. No. 350,536, Feb. 2, 1982, Pat. No. 4,480,092.

[51] Int. Cl.[5] ................ C07D 211/56; C07C 211/13; C07C 211/18
[52] U.S. Cl. ..................... 546/244; 546/16; 546/223; 564/306; 564/321; 564/455; 564/461; 564/512
[58] Field of Search ............. 564/306, 321, 455, 461, 564/512, 16, 223, 244

[56] References Cited

U.S. PATENT DOCUMENTS

| | | | |
|---|---|---|---|
| 2,267,204 | 12/1941 | Kyrides | 564/512 |
| 2,267,205 | 12/1941 | Kyrides | 564/512 |
| 2,393,825 | 1/1946 | Sinkus | 564/461 |
| 2,817,675 | 12/1957 | Hofer et al. | 564/461 |
| 2,844,599 | 7/1958 | Rendall et al. | 564/512 |
| 3,120,524 | 2/1964 | Godfrey | 564/512 |
| 3,151,160 | 9/1964 | Spivack | 564/368 |
| 3,565,941 | 2/1971 | Dick et al. | 564/487 |
| 4,126,640 | 11/1978 | Floyd | 564/512 |
| 4,480,092 | 10/1984 | Lai et al. | 544/113 |
| 4,547,538 | 10/1985 | Lai et al. | 524/100 |
| 4,605,743 | 8/1986 | Malz, Jr. et al. | 546/244 X |
| 4,607,104 | 8/1986 | Malz, Jr. et al. | 546/244 X |

FOREIGN PATENT DOCUMENTS 2070011 9/1981 United Kingdom .

OTHER PUBLICATIONS

Whitmore, Organic Chemistry, 2nd Ed., vol. 1, Pts. I, II, New York, Dover Publications, Inc., pp. 74, 77, 167.

*Primary Examiner*—Carolyn Elmore
*Assistant Examiner*—Mark W. Russell
*Attorney, Agent, or Firm*—Alfred D. Lobo

[57] ABSTRACT

A branched chain polyalkylene polyamine ("PAPA") having plural amine groups, including a secondary amine group intermediate terminal primary amine groups one of which is hindered, and having at least two carbon atoms between each group, is selectively reductively alkylated with a ketone. The reaction provides a convenient method for selectively reductively alkylating a PAPA having a hindered primary amine group, the method comprising contacting the PAPA with hydrogen and the ketone in the presence of a catalytically effective amount of a Group VIII metal on a catalyst support, at a pressure in the range from about 500–1000 psi and a temperature in the range from about 50° C. to about 200° C. for a period of time sufficient to preferentially alkylate the unhindered amine primary terminal amine group. The alkylation proceeds essentially without alkylating either the sterically hindered terminal primary amine group or the intermediate unhindered secondary amine group.

2 Claims, No Drawings

ALKYLATED POLYALKYLENE POLYAMINES AND PROCESS FOR SELECTIVE ALKYLATION

BACKGROUND OF THE INVENTION

This application is a continuation-in-part of Ser. No. 103,779 filed Oct. 2, 1987, now abandoned which is in turn a continuation-in-part of Ser. No. 786,765 filed Oct. 11, 1985, now abandoned, which is in turn a continuation-in-part of Ser. No. 664,901 filed Oct. 26, 1984, now issued as U.S. Pat. No. 4,547,538 which is in turn a continuation-in-part application of Ser. No. 350,536 filed Feb. 2, 1982 now issued as U.S. Pat. No. 4,480,092.

This invention relates to novel monoprimary-disecondary triamines and a method for their preparation from polyalkylene polyamines ("PAPA" for brevity). Such monoprimary-disecondary amines are useful as stabilizers for organic polymers, for use as curing agents for epoxy resins, and as starting materials for the preparation of polysubstituted piperazinones disclosed in the related prior case U.S. Pat. No. 4,547,538 issued Oct. 11, 1985, the disclosure of which is incorporated by reference thereto as if fully set forth herein.

Though it would seem that alkylation of a PAPA should be relatively straightforward, the reaction between alkyl halides and primary amines is not usually a feasible method for the preparation of an expected alkylated product amine, because the reaction does not stop after alkylation of the primary amine group, even if this is the only amine group in the amine reactant. Secondary amines are stronger bases than the amine reactant substrate, and therefore the secondary amine group preferentially attacks the alkyl halide yielding a tertiary amine. Therefore when both primary and secondary amine groups are present in the amine to be alkylated, a wide assortment of alkylated products is formed even under the most controlled conditions (see "Advanced Organic Chemistry Reactions, Mechanisms and Structures" by J. March, 3d edition, btm of pg. 365 John Wiley & Sons 1984.) For this reason, generally, alkylation with an alkyl halide is used where a tertiary amine is desired and one expects to effect complete alkylation of all amine groups. Even carefully controlled conditions generally give a mixture of alkylated products and is not favored even on a laboratory scale.

Alkylation of PAPA has been of considerable interest in the past and methods have been reported by Agnew, N. H. in Journal Chemical Society (London) Sec. C pg 203-208 (1966), and in U.S. Pat. No. 3,051,751. A process for selectively alkylating the secondary amino groups in a PAPA was disclosed in U.S. Pat. No. 3,565,941 and monotertiary-diprimary triamines are disclosed in U.S. Pat. No. 3,280,074.

A process is disclosed in U.S. Pat. No. 3,151,160 to Spivack for the preparation of tertiary-amino-alkylated primary amines in which the bridge nitrogen is tertiary. As Spivack states, even in this alkylation reaction where a very large excess of the reactant amine is used, this method is limited to only the simpler diamines because the inherent non-selective nature of the reaction leads to more or less random substitution of other replaceable hydrogens which results in drastic reduction in yields in the case of somewhat complex reactant amines. Spivack reiterates what has always been the problem with respect to the preparation of amines represented by structures which, on paper, look quite obvious. It is not obvious how one can go about obtaining an essentially pure amine by any type of alkylation reaction, even reductive alkylation.

By "essentially pure" I refer to an amine product of specified structure which is at least 90% pure.

The preparation of diprimary triamines having a secondary or tertiary N atom intermediate primary end groups is disclosed in U.S. Pat. No. 4,293,682. Because each of the C atoms adjacent the primary amine end groups (referred to as "N-adjacent C atom") is disubstituted, the primary amine end groups are hindered and such diprimary PAPA are not susceptible to the selective alkylation process of this invention in which the alkylated product is to have only one primary end group alkylated. Where a PAPA triamine has only one hindered primary amine end group, the other end group being unhindered, one might expect that only the unhindered amine group would be alkylated under conventional alkylation conditions, but both amine end groups are often alkylated, and maybe also the secondary amine.

U.S. Pat. No. 2,393,825 to Senkus teaches that a nitroamine may be prepared by reacting a primary or secondary amine with formaldehyde to form the corresponding N-hydroxymethyl, mono-, or dialkylamine, which is in turn reacted with an equimolar quantity of a secondary nitroparaffin to produce the desired nitroamine. This series of reactions may be illustrated as follows:

$$R^1NH_2 + HCHO \rightarrow R^1NHCH_2OH$$

the addition occurring at the terminal amine group, whether primary or secondary. If there were two amine groups, the addition reaction would be expected to occur at each amine group, though not to the same extent, particularly if one amine group was primary and the other was secondary.

Thereafter, the N-hydroxyalkylamine is reacted with a secondary nitroalkane, thus:

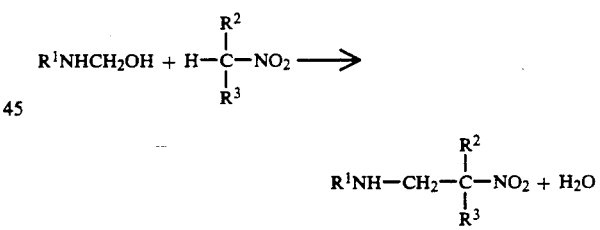

In an analogous manner, one may start with a secondary amine $R^1$-NH-R and HCHO to produce

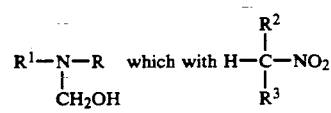

After hydrogenation of the nitroamine, the general formula of the polyamines which are made by the Senkus procedure is represented as follows:

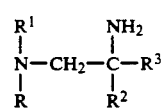

wherein R may be H, alkyl, or hydroxyalkyl; $R^1$ may be alkyl or hydroxyalkyl; and, $R^2$ and $R^3$ are alkyl.

In each case, the nitro group may be hydrogenated if the nitro group is on the tertiary C atom of a primary or secondary amine. But in Senkus' reduced compound (with the primary amine group), $R^1$ and R cannot both be H.

If the starting material is a diamine, rather than a primary or a secondary monoamine, and one tried to form a product with only one N-hydroxymethylamine group, one might use only a single mole of HCHO with the expectation that only one of the amine groups in the starting diamine would be hydroxymethylated. It would then be possible with this modification of the teaching of Senkus, to produce a compound which is similar to the precursor of our claimed PAPA.

Pursuing this modification of Senkus one would react nitropropane, formaldehyde and ethylenediamine as follows:

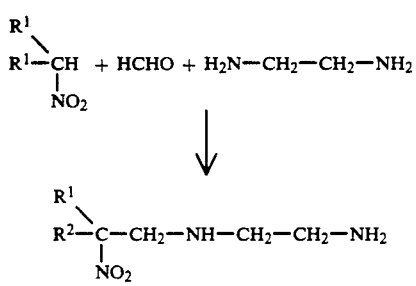

This nitroamine would then be hydrogenated to yield

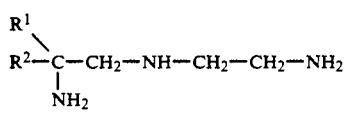

Because it is essential that the unhindered primary amine group be substituted, one would expect that the polyamine could be alkylated as suggested by Kyrides in U.S. Pat. Nos. 2,267,204 and 2,267,205.

The Kyrides polyamine is represented as follows:

which is formed by an alkylation reaction with a primary alkyl group, to introduce a long chain alkyl group in the structure. He defines: X is H or alkyl, R is an alkylene radical, and Y is alkyl. He states that both X and Y may preferably be the normal (straight chain) alkyl groups; however, forked or branched chain alkyl groups may be employed. (see '204, col 1, lines 43-46).

For our comparison purposes, X must be H. In the '204 and '205 patents, Y is a predominantly straight chain primary alkyl group, though he states (in '204) it may be branched. By "branched" he refers to a primary alkyl group derived from a primary alkyl halide, and not to a secondary alkyl group. In his example, 2-ethylhexyl is branched, but note that it is a primary alkyl group. The reason for his use of primary alkyl groups is because the secondary alkyl groups will not alkylate the amine in his method. The reaction does not proceed because of the steric hindrance at the halogen-bearing carbon atom.

We attempted to alkylate a large excess of the diamine, N-(2-amino-2-methylpropyl)-1,2-ethanediamine, obtained by hydrogenating the compound N-(2-methyl-2-nitropropyl)-1,2-ethanediamine having the structure:

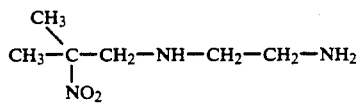

(made as described in our U.S. Pat. No. 4,698,446) with 1-chlorocyclohexane. There was no trace of the alkylated product in the reaction mass.

The difficulty of alkylating an amine with a secondary alkyl group is well known. For example, in Great Britain 2,070,011 to Jachimowicz, piperazine is alkylated with cyclohexene in the presence of a rhodium organometal catalyst and carbon monoxide, to obtain 1,4-dicylcohexylmethyl-piperazine as follows:

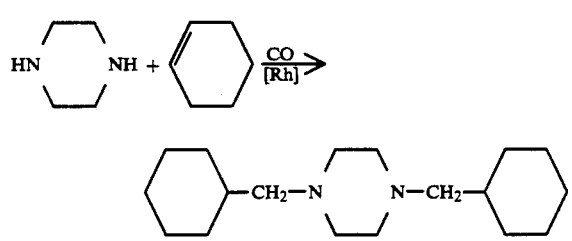

In the alkylated product, the resulting linkage is through $CH_2$, which is a primary linkage derived from the CO. Therefore this alkylation procedure would not result in our claimed compound.

Thus, the difficulty of obtaining any N-(2-propyl)-N'-(2-amino-2-methylpropyl)-1,2-diaminoethane, let alone essentially pure product, is evident. It will also be clear to those skilled in the art that unless the PAPA is essentially pure, its use for any practical application, is constricted.

The direct alkylation of a primary amine used in Kyrides '204 is the result of an N-alkylation reaction with a primary alkyl group. This reaction does not proceed with a secondary alkyl group as explained hereinabove. For example, our efforts to alkylate our precursor compound with 1-chlorocyclohexane does not result in the N-cyclohexylated product but with the formation of cyclohexene.

Thus, if one were to make a triamine with a Senkus starting material modified to include an alkyleneimine linkage, one would end up with a triamine with terminal primary amine groups one being hindered, and the other unable to be alkylated with a secondary alkyl group.

It appears that the '204 compounds can be readily modified. The isopropyl linkage between two amine groups in the '204 compound would appear to be readily substituted with an isobutyl linkage. However, it is essential that the methine C atom in the isopropyl linkage be substituted or it would not be the claimed compound, for example:

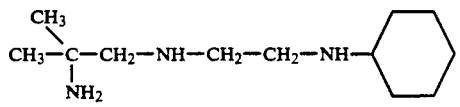

while the Kyrides compound would be written

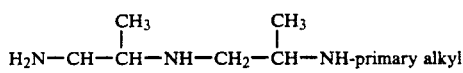

Specifically, in the N-2-ethylhexylethylene diamine (pg 2, line 46 in '204) the alkyl group is a primary alkyl group, while N-1-ethylhexyl is a secondary alkyl group.

If one was to alkylate to introduce the secondary alkyl group, with a rhodium organometal catalyst and CO, the CO will generate a $CH_2$ linking group making the alkyl group a primary one. To obtain the claimed compound, the alkyl group must be secondary.

It is important to note that each of the foregoing Kyrides references eschews making any suggestion that an essentially pure PAPA is produced, and of course, for use as insecticides or detergents, they need not be. One would also expect that the known catalytic alkylation with an olefin, such as is disclosed in Jachimowicz would provide a mixture of PAPA, not an essentially pure one.

Since both the hydrohalo elimination and alkylation reactions proceed concurrently, it is essential that the latter proceed preferentially if a reasonably pure, useful amine product is to be synthesized.

An appreciation of the magnitude of the difference between alkylation with a primary alkyl halide and a secondary alkyl halide may be derived from an examination of the rate constants for the substitution of alkyl bromides in 80% ethanol at 55° C. The second-order rate constant (because the reaction is predominantly second order) for isopropyl bromide is about 30 times slower than for ethyl bromide (see the textbook *Structure and Mechanism in Organic Chemistry* by C. K. Ingold, Table 24-1, pg 318, Cornell University Press).

The elimination reaction (bimolecular olefin formation from alkyl bromides) in ethyl alcohol at 25° C. has a rate constant of 11800 for isopropyl bromide, but only 2500 for ethyl bromide; this shows that elimination with a secondary halide is more than 4.5 times faster (see Ingold, supra, Table 31-7, pg 437).

In particular, we find that if the reaction of 1-chloro-2-methyl-2-aminopropane with N-(2-propyl)-1,2-diaminoethane yields any N-(2-propyl)-N'-(2-amino-2-methylpropyl)-1,2-diaminoethane at all, it is formed in so small an amount that it would not be feasible to separate it from its isomer N'-(2-amino-2-methylpropyl)-N'-(2-propyl)-1,2-diaminoethane, which is also formed, not to mention the many other alkylated products which are predominantly formed.

The reductive alkylation of PAPA is well known and described with numerous examples in the chapter entitled "Preparation of Amines by Reductive Alkylation" by W. S. Emerson in *Organic Reactions*, Vol 4, John Wiley & Sons, New York, N.Y. Examples are given for preparation (A) of tertiary amines from (i) secondary aliphatic amines and ketones, (ii) aryl alkyl amines and aliphatic aldehydes, (iii) aryl alkyl amines and ketones; etc., and, (B) of secondary amines by (i) reduction of Schiff's bases derived from aliphatic amines, and from aromatic amines, and (ii) reduction of primary aromatic amines, nitro or nitroso compounds and ketones, etc. In reductive alkylations with an aldehyde there is a wide scatter of side reaction because of the higher reactivity of an aldehyde than a ketone. There is no teaching that reductive alkylation with a ketone may result in alkylation only at a particular amino group substantially to the exclusion of all other amino groups, such result being obtained with a PAPA only by hindering one of the two primary amine groups and reacting with a ketone.

SUMMARY OF THE INVENTION

It has been discovered that an essentially pure alkylated polyalkylenepolyamine ("PAPA") can be obtained by a novel selective reductive alkylation reaction.

It has also been discovered that the reaction of a branched chain PAPA having plural amine groups including a secondary amine group intermediate terminal primary amine groups one of which is hindered, and having at least two carbon atoms between each group, may be selectively reductively alkylated with a ketone in an unexpectedly different manner from the known reaction of a PAPA with an aldehyde, wherein the PAPA has no hindered amine group.

It is therefore a general object of this invention to provide a process for selectively reductively alkylating a PAPA having a hindered primary amine group, comprising contacting said PAPA with hydrogen and a ketone in the presence of a catalytically effective amount of a Group VIII metal on a catalyst support, at a pressure in the range from about 500–1000 psi and a temperature in the range from about 50° C. to about 200° C., preferably using an inert solvent for the reactants, for a period of time sufficient to preferentially alkylate the unhindered amine primary terminal amine group, essentially without alkylating either the sterically hindered terminal primary amine group or the intermediate secondary amine group.

DETAILED DESCRIPTION OF PREFERRED EMBODIMENTS

Epoxy resins containing plural oxirane moieties in each chain are curable with polyamines among which the PAPA such as ethylene diamine, diethylene triamine, triethylene tetramine, and the like are effective at room temperature. However, such PAPA have short pot life, are difficult to use for one reason or the other including being too volatile, having unacceptably high toxicity, etc., and, the cured epoxy resins are often highly brittle and lack impact resistance.

To combat the foregoing drawbacks PAPA have been modified, for example, the short chain alkyl derivatives, or by reaction with fatty acids to form amino amides and amino polyamides. But such compounds are generally too viscous for easy use and do not offer the option of tailoring them easily. The process of this invention enlarges the scope of the types of alkylated PAPA which may be prepared and allows those which are specifically desired to be tailored substantially to the exclusion of forming unwanted compounds.

The process comprises reductively alkylating a particular class of PAPA, such as a N'-(aminoalkyl)-1,p-alkanediamine, N'-(aminoaryl)-1,p-alkanediamine, N'-(aminoaralkyl)-1,p-alkanediamine, and, N'-(aminocycloalky)-1,p-alkanediamine (hereafter collectively referred to as N'-(aminoalkyl/aryl/aralkyl/cycloalkyl)-1,p-alkanediamine, wherein 'p' corresponds to the number of C atoms in the diaminoalkane, and "2AD" for brevity) with an aliphatic, alicyclic or heterocyclic ketone in the presence of a Group VIII metal hydrogenation catalyst and an inert solvent for the reactants under hydrogenation conditions, by carrying out the reaction under elevated pressure and temperature to produce a N-(alkyl/piperidyl)- N'-(aminoalkyl/aryl/aralkyl/cycloalky)-1,p-alkanediamine which is the reductively alkylated ("2AAD" for brevity) product.

Preferred metals are Raney nickel, finely divided iron, cobalt, platinum, palladium, ruthenium, osmium, rhenium and rhodium, any one of which is to be supported on pumice, asbestos, kieselguhr, alumina, silica gel or charcoal. The amount of catalyst used depends upon the process conditions and also upon the reactants, from about 0.01% to about 10% by wt of the 2AD giving satisfactory results.

The ketone used may be any branched or unbranched aliphatic ketones, preferably having from 3 to about 20 carbon atoms, for example acetone, butanones, pentanones; alicyclic ketones, preferably having from 5 to about 8 carbon atoms, for example cyclopentanone, cyclohexanone, cyclooctanone; and, piperidinone which may be ring-substituted, preferably with $C_1$-$C_{20}$ alkyl and/or $C_5$-$C_8$ cycloalkyl spiro substituents, most preferably at the N-adjacent (2,6 positions) C atoms.

The most readily available preferred inert solvents are aliphatic and alicyclic hydrocarbons which are solvents for the reactants, but which resist reduction under the conditions of reaction. Particularly useful are the $C_1$-$C_{10}$ alkanes, such as hexane, and the alcohols such as the primary lower $C_1$-$C_6$ alcohols, though secondary alcohols such as isopropyl alcohol, or tertiary alcohols such as t-butyl alcohol may also be used.

The epoxy resins which can be cured at elevated temperatures using the 2AAD compounds of this invention are those polyepoxides possessing at least two oxirane groups which may be internal or terminal. The polyepoxides may be saturated or unsaturated, aliphatic, cycloaliphatic, aromatic or heterocyclic, and may be substituted such as with hydroxyl groups, ether radicals and the like. Further, the polyepoxides may be monomeric or polymeric. Such polyepoxides, and their preparation, are well known in the art.

The curing of the polyepoxides with the 2AAD curing agents may be accomplished by simply mixing the two components together, the 2AAD being present in an amount in the range from about 5 to about 35 parts per 100 parts by wt of epoxy resin. While the reaction between the two components occurs slowly at room temperature, acceleration of the cure is obtained if the mixture is heated to a temperature in the range from about 50°-100° C. for a period of time from about 0.5 to about 2 hr, and thereafter post-curing the reaction product for an additional period of time from about 2 to about 5 hr at elevated temperature above 100° C.

To cure a polyepoxide it is generally desirable that it be in a fluid condition when the 2AAD is added to facilitate obtaining a homogeneous mixture. If the polyepoxide is too viscous at room or casting temperature, it may be heated to reduce the viscosity, or a fugitive volatile liquid solvent may be added. During curing and post-curing the solvent escapes by evaporation. Typical of such volatile liquid solvents are ketones, such as acetone, methyl ethyl ketone, and the like; esters, such as ethyl acetate, butyl acetate and the like; ether alcohols such as methyl, ethyl or butyl ethers of ethylene glycol, and chlorinated hydrocarbons such as chloroform.

In addition to their use as curing agents for epoxy resins the 2AAD compounds may be cyclized to yield polysubstituted piperazinones which are UV stabilizers, and substituted oxo-piperazinyl-triazines as disclosed in our U.S. Pat. Nos. 4,480,092 and 4,639,479.

The foregoing reductive alkylation process may be effectively practiced with any PAPA having the general structure

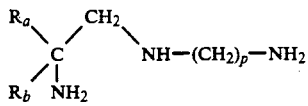

wherein, $R_a$ and $R_b$ independently represent alkyl having from 1 to 24 carbon atoms, aryl having from 6 to 10 carbon atoms, particularly phenyl, and aralkyl having from 7 to about 24 carbon atoms;

$R_a$ or $R_b$ may be cycloalkyl; or, $R_a$ and $R_b$ together when cyclized may be cycloalkyl having from 5 to about 7 carbon atoms; and, p represents an integer in the range from 2 to 10.

When the process is practiced with an aliphatic ketone having from 3 to about 20 carbon atoms, preferably a lower $C_3$-$C_9$ ketone, or a cycloaliphatic ketone having from 5 to about 20 carbon atoms and hydrogenation is effected over a Group VIII metal on a suitable catalyst support at a pressure in the range from about 500 psi to about 1000 psi and a temperature in the range from about 50° C. to about 200° C., no reaction product is isolated which is alkylated at either the intermediate amine group or the hindered terminal amine group.

The alkylated PAPA formed, referred to as the 2AAD compound, may be represented by the following general structure:

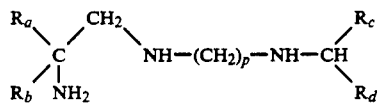

wherein, $R_c$ and $R_d$ independently represent branched or unbranched alkyl having from 1 to 24 carbon atoms, aralkyl having from 7 to about 24 carbon atoms;

$R_c$ or $R_d$, one or both may be cycloalkyl; or, $R_c$ and $R_d$ together when cyclized may be cycloalkyl having from 5 to about 7 carbon atoms, or, piperidyl which may be substituted at one or both of the N-adjacent carbon atoms in the piperidyl ring, each C atom with one, preferably two lower $C_1$-$C_6$ alkyl substituents, or, substituted at one C atom, preferably both N-adjacent C atoms with a cycloalkyl spiro substituent; and, $R_a$, $R_b$, and p have the same connotation as that given hereinabove.

Preparation of 2AAD Compound

In a typical reaction, the 2AAD compound is prepared from N-(2-amino-2-methylpropyl)-1,2-ethanediamine and a ketone selected to provide particularly desirable physical properties in the 2AAD, for example an agreeable odor, and minimal toxicity, or to provide the desired steric hindrance in the 2AAD compound if it is to be used for the preparation of polysubstituted piperazinones. The preparation of particular 2AAD compounds is illustrated in the following examples.

EXAMPLE 1

Preparation of N-(2-butyl)-N'-(2-amino-2-methylpropyl)-1,2-ethanediamine having the following structure

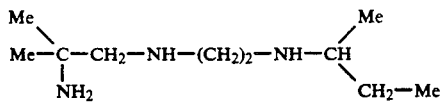

Me = methyl

A mixture of 146 g (1.1 moles) of N-(2-amino-2-methylpropyl)-1,2-ethanediamine, 84.4 g (1.17 moles) of 2-butanone, 300 ml methanol, and 3.0 g of 10% platinum on carbon were reacted in a 1 liter autoclave at 80° C. under 800 psi hydrogen pressure. After two hours the reaction mixture was cooled, then filtered to remove the catalyst. The filtrate was stripped to give 205.3 g of water-white clear liquid which was fractionally distilled under reduced pressure. The desired product recovered was found to weigh 144.5 g (69.5% yield), was about 95% pure, and has a boiling point (b p) of 62°-64° C./0.15 mm Hg.

The structure written hereinabove is supported by both proton nuclear magnetic resonance (NMR), and field desorption (FD) mass spectroscopic data.

EXAMPLE 2

Preparation of N-(4-methyl-2-pentyl)-N'-(2-amino-2-methylpropyl)-1,2-ethanediamine In an analogous manner, other dialkyl substituents may be substituted at the N position. For example, N-(4-methyl-2-pentyl)-N'-(2-amino-2-methylpropyl)-1,2-ethanediamine may be prepared from N-(2-amino-2-methylpropyl)-1,2-ethanediamine and 4-methyl-2-pentanone by reductive alkylation in propanol. The compound obtained in excellent yield is found to be more than 90% pure, and have a b p of 100°-109° C./0.3 mm Hg.

EXAMPLE 3

Preparation of N-(2-propyl)-N'-(2-amino-2-methylpropyl)-1,2-ethanediamine having the following structure

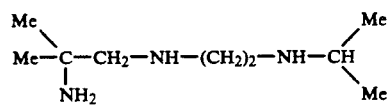

In a stirred autoclave place a mixture of 146 g of N-(2-amino-2-methylpropyl)-1,2-ethanediamine, 64 g acetone, 250 ml of methanol, and 7 g of 3% platinum on charcoal, and hydrogenate the mixture under 1500 psi H$_2$ pressure in a heated autoclave maintained at 150° C. After about 5 hr the reaction mixture is cooled, filtered to remove the catalyst, and concentrated. The desired product is obtained in 92% pure form which may be further purified by distilling at 90°-95° C./8 mm Hg to yield a colorless oil. The pure product boils at 96°-98° C./8 mm Hg.

The structure written above is supported by both proton NMR and FD mass spectroscopic data.

EXAMPLE 4

In an analogous manner, a cycloalkyl, a piperidyl (optionally substituted at the N-adjacent C atoms), an aryl or aralkyl substituent may be substituted at the N position as for example, by preparing N-cyclohexyl-N'-(2-amino-2-methylpropyl)-1,2-ethanediamine having the following structure:

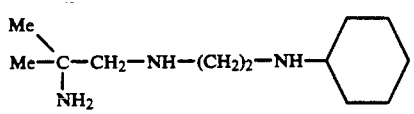

The desired compound is obtained by reacting N-(2-amino-2-methylpropyl)-1,2-ethanediamine with cyclohexanone in methanol in the presence of 10% Pt on carbon by hydrogenation at 80° C. under 800 psi. The desired compound is obtained in 98% pure form by fractionation at reduced pressure and has a b p of 96°-104° C. at 0.7 mm Hg.

In a manner analogous to that described immediately hereinabove, by reacting N-(2-amino-2-methylpropyl)-1,2-ethanediamine with piperidin-4-one, it is reductively alkylated to yield N-(4-piperidyl)-N'-(2-amino-2-methylpropyl)-1,2-ethanediamine; and, 2,2,6,6-piperidin-4-one is reductively alkylated to yield N-(2,2,6,6-tetramethyl-4-piperidyl)-N'-(2-amino-2-methylpropyl)-1,2-ethanediamine having the structure:

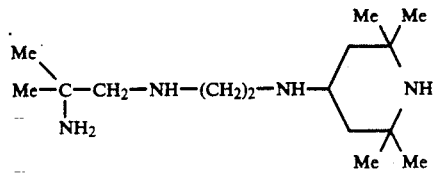

In a manner analogous to that described herein above, the following 2AAD compounds are prepared:

N-(2-propyl)-N'-(2-amino-2-ethylbutyl)-1,2-ethanediamine;

N-cyclohexyl-N'-(2-amino-2-ethylbutyl)-1,3-propanediamine;

N-(4-piperidyl)-N'-(2-amino-2-methylpropyl)-1,2-ethanediamine;

N-(2,2,6,6-tetramethyl-4-piperidyl)-N'-(2-amino-2-methylpropyl)-1,2-ethanediamine;

N-(2-octyl)-N'-(2-amino-2-ethylbutyl)-6-hexanediamine;

N-(2-propyl)-N'-(2-amino-2-2-diphenylethyl)-1,2-ethanediamine;

N-cyclohexyl-N'-(2-amino-2-2-diphenylethyl)-1,6-hexanediamine;

N-(2-propyl)-N'-(1-aminocyclohexylmethyl)-1,2-ethanediamine; and,

N-cyclohexyl-N'-(1-aminocyclohexylmethyl)-1,6-hexanediamine.

It will now be evident that a wide variety of substituents may be made in the 2AAD compounds formed, and the effect of each can be judged by simple trial and error until the optimum properties are obtained for the purpose at hand.

Of course, such optimum properties of a PAPA can best be judged only with an essentially pure mass of the desired PAPA which is free from any cyclic PAPA, and free from those acyclic PAPA alkylated at secondary amino groups which result in unwanted PAPA. We know of no process, other than the one we have disclosed hereinabove, which will provide the essentially pure mass of PAPA.

Note, that in the foregoing specification, the term N-(alkyl/piperidyl) is used to identify the PAPA which has been alkylated at the unhindered primary amine group with either an alkyl group or a piperidyl group as illustrated in the examples provided.

We claim:

1. An essentially pure alkylated polyalkylenepolyamine having the structure

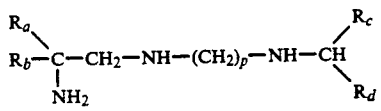

wherein, $R_a$ and $R_b$ independently represent alkyl having from 1 to 24 carbon atoms, and aralkyl having from 7 to about 20 carbon atoms or cycloalkyl; or, $R_a$ and $R_b$ together when cyclized form a cycloalkyl having from 5 to about 7 carbon atom;

$R_c$ and $R_d$ independently represent branched or unbranched alkyl having from 1 to 24 carbon atoms, aralkyl having from 7 to about 20 carbon atoms or cycloalkyl;

$R_c$ and $R_d$ together when cyclized form a cycloalkyl having from 5 to about 7 carbon atoms, unsubstituted piperidyl or substituted piperidyl wherein said substituents are one or more alkyl or spiro cycloalkyl at one or both of the N-adjacent carbon atoms; and, p represents an integer in the range from 2 to 10.

2. The essentially pure composition of claim 1, including:

N-(2-propyl)-N'-(2-amino-2-ethylbutyl)-1,2-ethanediamine;

N-cyclohexyl-N'-(2-amino-2-ethylbutyl)-1,3-propanediamine;

N-(2-octyl)-N'-(2-amino-2-ethylbutyl)-1,6-hexanediamine;

N-(2-butyl)-N'-(2-amino-2-methylpropyl)-1,2-ethanediamine;

N-(4-methyl-2-pentyl)-N'-(2-amino-2-methylpropyl)-1,2-ethanediamine;

N-(2-propyl)-N'-(2-amino-2-methylpropyl)-1,2-ethanediamine;

N-cyclohexyl-N'-(2-amino-2-methylpropyl)-1,2-ethanediamine;

N-(4-piperidyl)-N'-(2-amino-2-methylpropyl)-1,2-ethanediamine;

N-(2,2,6,6-tetramethyl-4-piperidyl)-N'-(2-amino-2-methylpropyl)-1,2-ethanediamine;

N-(2-propyl)-N'-((1-aminocyclohexyl)methyl)-1,2-ethanediamine; or,

N-cyclohexyl-N'-((1-aminocyclohexyl)methyl)-1,6-hexanediamine.

* * * * *